United States Patent
Sakanishi

(10) Patent No.: US 10,844,034 B2
(45) Date of Patent: Nov. 24, 2020

(54) NONIONIC SURFACTANT

(71) Applicant: DAICEL CORPORATION, Osaka (JP)

(72) Inventor: Yuichi Sakanishi, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 16/308,105

(22) PCT Filed: Apr. 21, 2017

(86) PCT No.: PCT/JP2017/016051
§ 371 (c)(1),
(2) Date: Dec. 7, 2018

(87) PCT Pub. No.: WO2017/212803
PCT Pub. Date: Dec. 14, 2017

(65) Prior Publication Data
US 2019/0300495 A1 Oct. 3, 2019

(30) Foreign Application Priority Data

Jun. 10, 2016 (JP) .................. 2016-115801

(51) Int. Cl.
| C07D 311/20 | (2006.01) |
| B01F 17/00 | (2006.01) |
| C11D 1/72 | (2006.01) |
| A61K 8/49 | (2006.01) |
| A61Q 19/10 | (2006.01) |
| A61K 8/39 | (2006.01) |
| A61Q 5/02 | (2006.01) |
| A61K 8/86 | (2006.01) |

(52) U.S. Cl.
CPC ............. *C07D 311/20* (2013.01); *A61K 8/39* (2013.01); *A61K 8/49* (2013.01); *A61K 8/86* (2013.01); *A61Q 5/02* (2013.01); *A61Q 19/10* (2013.01); *B01F 17/0021* (2013.01); *C11D 1/72* (2013.01)

(58) Field of Classification Search
CPC .................................................. C07D 311/20
See application file for complete search history.

(56) References Cited

U.S. PATENT DOCUMENTS

| 6,005,126 A | 12/1999 | Ishitobi et al. |
| 2002/0035238 A1 | 3/2002 | Nakamura et al. |
| 2009/0239958 A1 | 9/2009 | Sakahishi et al. |

FOREIGN PATENT DOCUMENTS

| EP | 2103674 A2 | 9/2009 | |
| JP | 7-126690 A | 5/1995 | |
| JP | 11-124563 A | 5/1999 | |
| JP | 2001-114720 A | 4/2001 | |
| JP | 2004-285099 A | 10/2004 | |
| WO | WO-2008014979 A2 * | 2/2008 | ............. C07H 21/02 |

OTHER PUBLICATIONS

International Search Report, issued in PCT/JP2017/016051, dated May 30, 2017.
Written Opinion of the International Searching Authority, issued in PCT/JP2017/016051, dated May 30, 2017.
Extended European Search Report, dated Dec. 18, 2019, for European Application No. 17809985.9.

* cited by examiner

*Primary Examiner* — John S Kenyon
(74) *Attorney, Agent, or Firm* — Birch, Stewart, Kolasch & Birch, LLP

(57) ABSTRACT

A nonionic surfactant that is environmentally friendly, has excellent surface active power (emulsifying power and solubilizing power), and is capable of stably maintaining the excellent surface active power for a long time is provided. A nonionic surfactant of the present invention contains polyglycerol monoether represented by the formula (1), wherein a ring Z represents a condensed ring of an aromatic hydrocarbon ring having 6 to 14 carbon atoms and a 3 to 6-membered heterocycle containing an oxygen atom as a heteroatom; $R^1$ is a substituent bonded to the ring Z and represents an aliphatic hydrocarbon group having 14 to 25 carbon atoms; the ring Z optionally has one or more substituents other than $R^1$; and n is an average number of monomers of glycerol and represents 2 to 20.

[Formula 1]

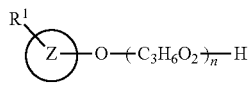

(1)

7 Claims, No Drawings

NONIONIC SURFACTANT

TECHNICAL FIELD

The present invention relates to a nonionic surfactant showing an excellent emulsifying effect on various oils and solvents. The present application claims priority from Japanese patent application JP 2016-115801 filed on Jun. 10, 2016, which is hereby incorporated by reference.

BACKGROUND ART

Alkylphenol ethoxylates such as octylphenol ethoxylate and nonylphenol ethoxylate, which are produced by addition polymerization of alkyl phenols with ethylene oxide, are aromatic nonionic surfactants having excellent surface active power. Recently, there have been concerns that these compounds and decomposition products thereof (such as alkyl phenols and short-chain alkylphenol ethoxylates) or oxides thereof have an adverse effect on the environment and the ecosystem.

Given the above situation, aliphatic nonionic surfactants having a polyalkylene oxide chain as a hydrophilic group, which are produced by addition polymerization of aliphatic alcohols with an alkylene oxide having 2 to 4 carbon atoms such as ethylene oxide, have been used in fields such as a field of a detergent where consideration needs to be given to the environment and the ecosystem (see Patent Literature 1).

However, there has been a problem in that the surface active power of the aliphatic nonionic surfactants tends to decrease with time. This is because, when the surfactants contain an aliphatic hydrocarbon group as a hydrophobic group, an association force between a polyalkylene oxide chain as a hydrophilic group and water is weak, and thus hydrophilicity (or affinity for water) tends to decrease with time.

That is, under the present circumstances, a nonionic surfactant that is environmentally friendly, has an excellent surface active effect equivalent to those of alkylphenol ethoxylates such as octylphenol ethoxylate and nonylphenol ethoxylate, and is capable of stably maintaining the excellent surface active power for a long time has not been found.

CITATION LIST

Patent Literature

Patent Literature 1: Japanese Patent Laid-Open No. 7-126690

SUMMARY OF INVENTION

Technical Problem

Accordingly, it is an object of the present invention to provide a nonionic surfactant that is environmentally friendly, has excellent surface active power (emulsifying power and solubilizing power), and is capable of stably maintaining the excellent surface active power for a long time.

Solution to Problem

The present inventors conducted an extensive study to achieve the above object, and consequently found out the following: While a nonionic surfactant having a polyalkylene oxide chain as a hydrophilic group is a compound that shows hydrophilicity by a hydrogen bond with a water molecule, which is easily affected by a temperature and easily makes the hydrophilicity low according to the temperature, a nonionic surfactant having a polyglycerol chain as a hydrophilic group shows stable hydrophilicity at a wide range of temperatures and is capable of preventing a decrease in the surface active power with time. A nonionic surfactant having a polyglycerol chain as a hydrophilic group and an aryl group containing an aliphatic hydrocarbon group having a specific chain length as a hydrophobic group shows far better surface active power and is much more capable of preventing a decrease in the surface active power with time as compared to a nonionic surfactant having a polyglycerol chain as a hydrophilic group and an aliphatic hydrocarbon group as a hydrophobic group. The present invention was completed by conducting further studies based on these findings.

That is, the present invention provides a nonionic surfactant containing polyglycerol monoether represented by the following formula (1):

[Formula 1]

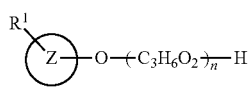

(1)

wherein a ring Z represents a condensed ring of an aromatic hydrocarbon ring having 6 to 14 carbon atoms and a 3 to 6-membered heterocycle containing an oxygen atom as a heteroatom; $R^1$ is a substituent bonded to the ring Z and represents an aliphatic hydrocarbon group having 14 to 25 carbon atoms; the ring Z optionally has one or more substituents other than $R^1$; and n is an average number of monomers of glycerol and represents 2 to 20.

The present invention further provides the nonionic surfactant in which $R^2$ is a substituent bonded to a heterocycle moiety of the ring Z, the ring Z being a condensed ring of an aromatic hydrocarbon ring having 6 to 14 carbon atoms and a 3 to 6-membered heterocycle containing an oxygen atom as a heteroatom.

The present invention further provides the nonionic surfactant in which the polyglycerol monoether represented by the formula (1) is a compound represented by the following formula (1-1) or (1-2):

[Formula 2]

-continued

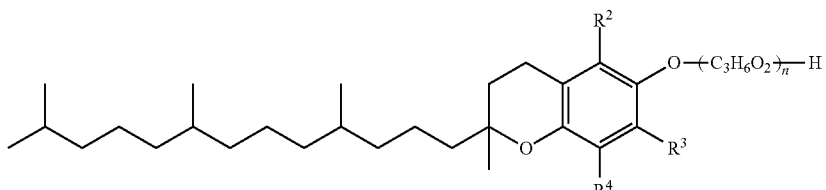

(1-1)

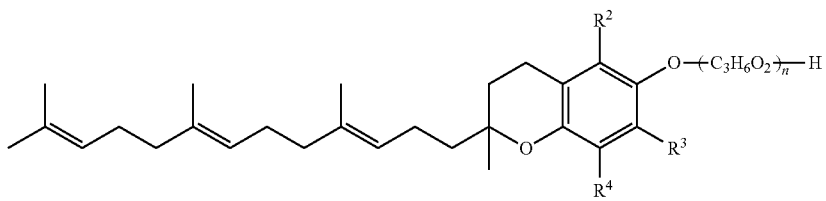

(1-2)

wherein $R^2$, $R^3$, and $R^4$ are the same or different from each other, and each represents a hydrogen atom, an alkyl group having 1 to 5 carbon atoms, or a hydroxy group; and n is an average number of monomers of glycerol and represents 2 to 20.

The present invention further provides the nonionic surfactant for use as a detergent.

The present invention further provides the nonionic surfactant for use as an emulsifier.

The present invention further provides the nonionic surfactant for use as an emulsifier for emulsion polymerization. The present invention further provides the nonionic surfactant for use as a solubilizing agent.

That is, the present invention relates to the following matters. [1] A nonionic surfactant containing polyglycerol monoether represented by the above formula (1), wherein a ring Z represents a condensed ring of an aromatic hydrocarbon ring having 6 to 14 carbon atoms and a 3 to 6-membered heterocycle containing an oxygen atom as a heteroatom; $R^1$ is a substituent bonded to the ring Z and represents an aliphatic hydrocarbon group having 14 to 25 carbon atoms; the ring Z optionally has one or more substituents other than $R^1$; and n is an average number of monomers of glycerol and represents 2 to 20.

[2] The nonionic surfactant according to [1], wherein $R^1$ is a substituent bonded to a heterocycle moiety of the ring Z, the ring Z being a condensed ring of an aromatic hydrocarbon ring having 6 to 14 carbon atoms and a 3 to 6-membered heterocycle containing an oxygen atom as a heteroatom.

[3] The nonionic surfactant according to [1] or [2], wherein the aromatic hydrocarbon ring forming the ring Z has 6 to 10 carbon atoms.

[4] The nonionic surfactant according to any one of [1] to [3], wherein the aromatic hydrocarbon ring forming the ring Z is a benzene ring or a naphthalene ring.

[5] The nonionic surfactant according to any one of [1] to [4], wherein the heterocycle forming the ring Z is a 4 to 6-membered heterocycle, a 5 or 6-membered heterocycle, or a 6-membered heterocycle.

[6] The nonionic surfactant according to any one of [1] to [5], wherein the number of carbon atoms of the aliphatic hydrocarbon group represented by $R^1$ has an upper limit of 23, 22, or 20 and a lower limit of 15 or 16.

[7] The nonionic surfactant according to any one of [1] to [6], wherein the substituent other than $R^1$ of the ring Z is at least one selected from a group consisting of an alkyl group having 1 to 5 carbon atoms, a halogen atom, an oxo group, a hydroxy group, an alkoxy group having 1 to 5 carbon atoms, a carboxyl group, and an alkoxy carbonyl group having 1 to 5 carbon atoms.

[8] The nonionic surfactant according to any one of [1] to [7], wherein the substituent other than $R^1$ of the ring Z is an alkyl group having 1 to 5 carbon atoms.

[9] The nonionic surfactant according to any one of [1] to [8], wherein the number of the substituent other than $R^1$ of the ring Z is 0 to 12, 1 to 8, 2 to 6, or 3 to 5.

[10] The nonionic surfactant according to any one of [1] to [9], wherein n is 5 to 20 or 8 to 15.

[11] The nonionic surfactant according to any one of [1] to [10], wherein the polyglycerol monoether represented by the formula (1) is a compound represented by the above formula (1-1) or (1-2), wherein $R^2$, $R^3$, and $R^4$ are the same or different from each other, and each represents a hydrogen atom, an alkyl group having 1 to 5 carbon atoms, or a hydroxy group; and n is an average number of monomers of glycerol and represents 2 to 20.

[12] The nonionic surfactant according to any one of [1] to [11], for use as a detergent.

[13] The nonionic surfactant according to any one of [1] to [12], for use as an emulsifier.

[14] The nonionic surfactant according to any one of [1] to [13], for use as an emulsifier for emulsion polymerization.

[15] The nonionic surfactant according to any one of [1] to [14], for use as a solubilizing agent.

Advantageous Effects of Invention

The nonionic surfactant of the present invention contains a combination of a specific hydrophilic group and a specific hydrophobic group, and therefore prevents a change in hydrophilicity involved with a temperature change, shows an excellent surface active effect (emulsifying power and solubilizing power), which is equivalent to those of alkylphenol ethoxylates such as octylphenol ethoxylate and nonylphenol ethoxylate, on various oils such as a mineral oil, a vegetable oil, and a silicone oil, solvents, and synthetic resins, and is capable of stably maintaining the excellent surface active power for a long time (for example, for 30 days or more, preferably for 40 days or more, more preferably for 60 days or more). In addition to that, the above nonionic surfactant is environmentally friendly. Accordingly, the nonionic surfactant of the present invention is useful for a detergent, an emulsifier, an emulsifier for emulsion polymerization, or a solubilizing agent.

DESCRIPTION OF EMBODIMENTS

[Nonionic Surfactant]

A nonionic surfactant of the present invention contains polyglycerol monoether represented by the following formula (1). In the following formula (1), a ring Z having a substituent $R^1$ is a hydrophobic group, and a polyglycerol chain is a hydrophilic group.

[Formula 3]

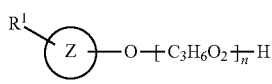

(1)

wherein the ring Z represents a condensed ring of an aromatic hydrocarbon ring having 6 to 14 carbon atoms and a 3 to 6-membered heterocycle containing an oxygen atom as a heteroatom; $R^1$ is a substituent bonded to the ring Z and represents an aliphatic hydrocarbon group having 14 to 25 carbon atoms; the ring Z optionally has one or more substituents other than $R^1$; and n is an average number of monomers of glycerol and represents 2 to 20.

The aromatic hydrocarbon ring having 6 to 14 carbon atoms forming the ring Z is preferably an aromatic hydrocarbon ring having 6 to 10 carbon atoms, and examples thereof include a benzene ring and a naphthalene ring.

The 3 to 6-membered heterocycle containing an oxygen atom as a heteroatom forming the ring Z is a heterocycle containing at least an oxygen atom as a heteroatom and may contain a heteroatom other than the oxygen atom. Examples of such a heterocycle include a 3-membered ring such as an oxirane ring; a 4-membered ring such as an oxetane ring; a 5-membered ring such as a furan ring, a tetrahydrofuran ring, an oxazole ring, an isoxazole ring, a γ-butyrolactone ring; and a 6-membered ring such as a 4-oxo-4H-pyrane ring, a tetrahydropyran ring, and a morpholine ring.

$R^1$ represents the aliphatic hydrocarbon group having 14 to 25 carbon atoms, and an upper limit of the number of carbon atoms thereof is preferably 23, particularly preferably 22, most preferably 20. A lower limit of the number of carbon atoms thereof is preferably 15, particularly preferably 16. The aliphatic hydrocarbon group contains a straight-chain or branched-chain aliphatic hydrocarbon group. In the present invention, particularly the branched-chain aliphatic hydrocarbon group (branched-chain saturated or unsaturated aliphatic hydrocarbon group) is preferable in terms of water solubility, and more particularly, a branched-chain alkyl group or a branched-chain alkenyl group is preferable.

$R^1$ is the substituent bonded to the ring Z and may be bonded to the aromatic hydrocarbon ring moiety of the ring Z, the ring Z being a condensed ring of an aromatic hydrocarbon ring having 6 to 14 carbon atoms and a 3 to 6-membered heterocycle containing an oxygen atom as a heteroatom, or may be bonded to the heterocycle moiety. It is preferable that in the present invention, particularly $R^1$ is bonded to the heterocycle moiety of the ring Z.

The ring Z optionally has one or more substituents other than $R^1$. Examples of other substituents include an alkyl group having 1 to 5 carbon atoms, a halogen atom, an oxo group, a hydroxy group, an alkoxy group having 1 to 5 carbon atoms, a carboxyl group, an alkoxy carbonyl group having 1 to 5 carbon atoms. These can be contained singly or in combinations of two or more thereof. The number of other substituents of the ring Z is not limited to a particular number, and is, for example, 0 to 12, preferably 1 to 8, more preferably 2 to 6, further preferably 3 to 5.

As the hydrophobic group contained in polyglycerol monoether represented by the formula (1), a group represented by the following formula (z-1) or (z-2) is preferable in terms of being environmentally friendly and being particularly excellent in the surface active power, and more particularly, a residue formed by removing a hydroxy group from a structural formula of tocopherol or tocotrienol is preferable. A wavy line part of the following formula is bonded to a polyglycerol chain as a hydrophilic group.

[Formula 4]

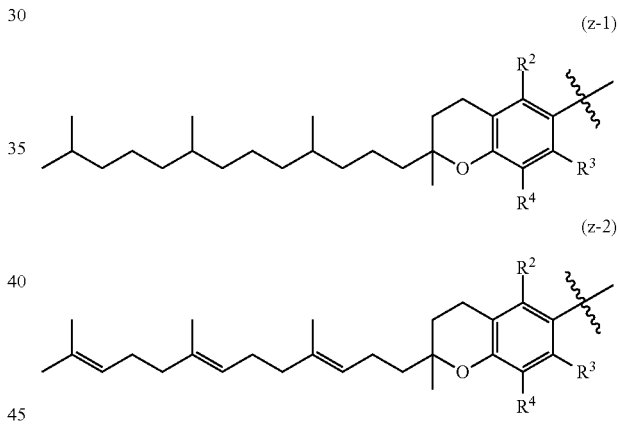

wherein $R^2$, $R^3$, and $R^4$ are the same or different from each other, and each represents a hydrogen atom, an alkyl group having 1 to 5 carbon atoms, or a hydroxy group.

Accordingly, as polyglycerol monoether represented by the formula (1), a compound represented by the following formula (1-1) or (1-2) is preferable, and more particularly, polyglycerol mono-tocopheryl ether or polyglycerol mono-tocotrienyl ether is preferable.

[Formula 5]

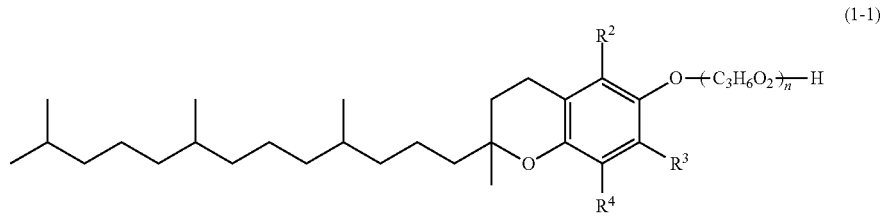

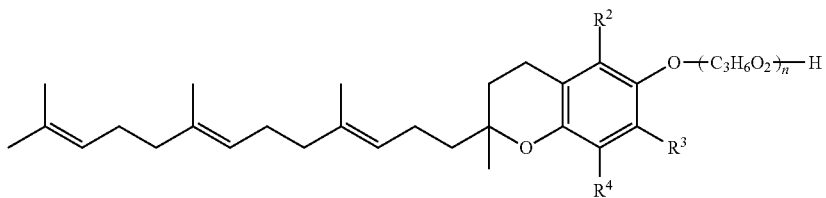

(1-2)

wherein $R^2$, $R^3$, and $R^4$ are the same or different from each other, and each represents a hydrogen atom, an alkyl group having 1 to 5 carbon atoms, or a hydroxy group; and n is an average number of monomers of glycerol and represents 2 to 20.

Examples of the alkyl group having 1 to 5 carbon atoms include a methyl group, an ethyl group, a propyl group, an isopropyl group, a butyl group, an isobutyl group, a s-butyl group, a t-butyl group, and a pentyl group.

In the above formula (1), formula (1-1), and formula (1-2), $C_3H_6O_2$ inside the parentheses preferably has at least one of the structures represented by the following formula (a) or (b).

  (a)

  (b)

In the above formula (1), formula (1-1), and formula (1-2), n represents the average number of monomers of glycerol and is 2 to 20. n is preferably 5 to 20, particularly preferably 8 to 15.

The nonionic surfactant of the present invention may contain polyglycerol monoethers represented by the above formula (1) singly or in combinations of two or more thereof.

The nonionic surfactant of the present invention can be produced by various methods, and examples of the methods include
(i) addition polymerization of the alcohol represented by the following formula (2) (such as tocopherol and tocotrienol) with epichlorohydrin,

[Formula 6]

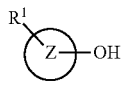  (2)

wherein the ring Z and $R^1$ are the same as above; and the ring Z optionally has one or more substituents other than $R^1$, and
(ii) addition polymerization of the alcohol represented by the above formula (2) with glycidol.

In the present invention, particularly the method (ii) is preferably employed from a safety and hygiene aspect and an environmental aspect as this method can prevent a chlorine atom derived from a raw material from getting mixed with a reaction product. According to the method, polyglycerol monoether represented by the formula (1) can be selectively produced. With the nonionic surfactant which is produced by the above method and contains high-purity polyglycerol monoether represented by the formula (1), its amount used can be reduced, which can consequently ease an increasing pressure to the environment caused by an excessive use of surfactants and also prevent users from getting rough dry skin, as compared to a nonionic surfactant containing polyglycerol monoether represented by the formula (1) in a low concentration.

The method for adding glycidol to the alcohol represented by the above formula (2) can be performed by a method in which an alkaline catalyst is added to the alcohol represented by the above formula (2) to produce an alkoxide, and thereafter, glycidol is added to carry out a dehydration condensation reaction.

The alkaline catalyst used in the present invention is preferably a compound from which a remainder after producing the alkoxide from the alcohol represented by the formula (2) is easily removed. Examples of the alkaline catalyst include basic compounds in which a proton moiety of a protic solvent is substituted with an alkali metal or an alkaline-earth metal cation (such as potassium hydroxide, sodium hydroxide, lithium hydroxide, magnesium hydroxide, calcium hydroxide, sodium methoxide, sodium ethoxide, potassium methoxide, potassium ethoxide, butoxypotassium, and butoxysodium), basic compounds in which a saturated hydrocarbon moiety is substituted with an alkali metal or an alkaline-earth metal cation (such as butyllithium, methyllithium, and ethyllithium), and basic metals (such as sodium, potassium, and lithium). These can be used singly or in combinations of two or more thereof.

An amount used of the alkaline catalyst is, for example, 4 to 40 mol %, preferably 5 to 30 mol %, relative to the alcohol represented by the above formula (2). When the amount used of the alkaline catalyst is less than 4 mol %, glycidol tends to undergo self-polymerization and produce polyglycerol as a by-product before reacting with an alkoxide. Further, when the amount used of the alkaline catalyst is more than 40 mol %, a large amount of reduced products tends to be produced as a by-product.

In the above reaction, the alkaline catalyst is added to the alcohol represented by the above formula (2) preferably before an addition of glycidol. The alkaline catalyst can be added to a reaction system all at once or a little at a time. Further, after the alkaline catalyst is added, the alkoxide is preferably produced while distilling water by heating or heating under a reduced pressure as this can facilitate a transformation of the alcohol represented by the above formula (2) into the alkoxide.

The dehydration condensation reaction of the alkoxide with glycidol is preferably carried out under an inert gas-flushed atmosphere (such as under a nitrogen gas-flushed atmosphere) to prevent hydrolysis of the alkoxide. The reason is that if the hydrolysis of the alkoxide is proceeded, polyglycerol as a by-product tends to be produced using an alkali compound as an initiator resulted from the hydrolysis. A pressure may be applied during the reaction as necessary.

A reaction temperature of the above reaction is, for example, 0 to 150° C., preferably 60 to 140° C., more preferably 80 to 130° C. When the reaction temperature is less than 0° C., it is difficult to stir the reaction system, which inhibits the reaction from proceeding in some cases. When the reaction temperature is more than 150° C., glycidol tends to undergo self-polymerization and produce polyglycerol as a by-product before reacting with the alkoxide.

When the above reaction is carried out, a low-boiling compound or an inert solvent each of which has a low reactivity with glycidol may be added for the purpose of preventing the reaction temperature from going up and lowering a viscosity of a reaction liquid. Examples of such a compound or a solvent include acetone, ethyl acetate, butyl acetate, hexane, toluene, and xylene. These can be used singly or in combinations of two or more thereof.

After the reaction is completed, a resultant reaction product can be separated and purified by a separation means such as filtration, concentration, distillation, extraction, crystallization, adsorption, recrystallization, and column chromatography or a combination of these separation means.

For example, when the nonionic surfactant of the present invention is produced by the above method (ii), a reaction product contains an alkaline catalyst or a salt thereof. In this case, it is preferable that the purification is carried out to remove such contents from the reaction product from the safety and hygiene aspect and the environmental aspect.

It is preferable that the purification is carried out in such a manner that the alkaline catalyst is neutralized with an acid, and a precipitated salt of an alkali metal or an alkaline earth metal is removed by filtration.

Examples of the acid used for neutralization of the alkaline catalyst include an inorganic acid such as a phosphoric acid, a sulfuric acid, a hydrochloric acid, and a nitric acid; and an organic acid such as a formic acid, an acetic acid, a butyric acid, and a valeric acid. These can be used singly or in combinations of two or more thereof. In the present invention, particularly the inorganic acid is preferably used, and more particularly, a hydrochloric acid and/or a phosphoric acid are preferably used.

After the neutralization of the alkaline catalyst with an acid, it is preferable that distillation is carried out on the reaction product to remove a low-boiling component before carrying out the filtration. The distillation is preferably carried out under an inert gas-flushed atmosphere or under a reduced pressure to prevent a by-product from being produced by oxidation, etc.

Further, when the reaction product has a high viscosity, the filtration may be carried out after the reaction product is diluted with a solvent which is a poor solvent of the salt and a good solvent of polyglycerol monoether represented by the formula (1) to lower the viscosity (for example, when a filter press of which filtration equipment is capable of applying a pressure of 4 kg/cm$^2$ is used, the filtration may be carried out after the viscosity of the reaction product is lowered to 30 cps or less) for the purpose of improving a filtration efficiency.

Examples of the solvent used for diluting the reaction product include a polar solvent such as alcohols; and a nonpolar solvent such as pentane, hexane, octane, benzene, acetone, ethyl acetate, and diethyl ether. These can be used singly or in combinations of two or more thereof.

As the solvent, particularly the polar solvent is preferable, and more particularly, the alcohols are preferable. The alcohols include a saturated aliphatic alcohol (such as methanol and ethanol), an unsaturated aliphatic alcohol, and an aromatic alcohol (such as phenol). The alcohols also include alcohols having a straight chain, a branched chain, and a cyclic structure. The alcohols further include a polyhydric alcohol such as a dihydric alcohol. In the present invention, an alcohol having 1 to 8 carbon atoms is preferable and an alcohol having 1 to 4 carbon atoms is particularly preferable.

Purification may be further carried out on the nonionic surfactant of the present invention produced by the above production method as necessary. Examples of a purification method include (A) a deodorization method of deodorizing with water steam by blowing a saturated superheated steam under a reduced pressure and (B) a decolorization method including bleaching with sodium hypophosphite or hydrogen peroxide.

The nonionic surfactant according to the present invention contains at least polyglycerol monoether represented by the above formula (1). A proportion of polyglycerol monoether represented by the formula (1) is, for example, 75 weight % or more, preferably 80 weight % or more, particularly preferably 85 weight % or more, most preferably 90 weight % or more, relative to a total amount of non-volatile contents (100 weight %) of the nonionic surfactant according to the present invention. An upper limit of the proportion is 100 weight %.

The nonionic surfactant according to the present invention may contain polyglycerol, and a content of polyglycerol is, for example, 20 weight % or less, preferably 10 weight % or less, relative to the total amount of non-volatile contents (100 weight %) of the nonionic surfactant according to the present invention. When the content of polyglycerol exceeds the above range, the nonionic surfactant according to the present invention tends to have low dispersibility to water.

The nonionic surfactant according to the present invention may further contain polyglycerol polyether such as polyglycerol diether and polyglycerol triether, and a content of polyglycerol polyether (when two or more are contained, the total amount thereof) is, for example, 5 weight % or less, preferably 1 weight % or less, relative to the total amount of non-volatile contents (100 weight %) of the nonionic surfactant according to the present invention. When the content of polyglycerol polyether exceeds the above range, the nonionic surfactant according to the present invention tends to have low dispersibility to water.

The nonionic surfactant according to the present invention has excellent solubility to water. Thus, even if the nonionic surfactant according to the present invention contains water (for example, even if the water is contained in a ratio [polyglycerol monoether represented by the formula (1): water (weight ratio)] of 70:30 to 99.9:0.1 relative to polyglycerol monoether represented by the formula (1)), its external appearance and uniformity can be satisfactorily maintained.

The nonionic surfactant according to the present invention may further contain one or more other components without losing the advantageous effects of the present invention. Examples of other components include a surfactant other than polyglycerol monoether represented by the formula (1) (such as sodium polyoxyethylene alkyl ether sulfate having an average number of moles added of 5 to 10, sucrose fatty acid ester, glycerol fatty acid ester, sorbitan fatty acid ester, propylene glycol fatty acid ester, polyoxyethylene sorbitan fatty acid ester, fatty acid monoethanolamide, polyoxyethylene alkyl ether, polyoxyethylene alkyl phenyl ether, a carboxy betaine-type amphoteric surfactant, an imidazolinium-type amphoteric surfactant, a sulfobetaine-type amphoteric surfactant, and an alanine-type amphoteric surfactant), a builder (such as sodium pyrophosphate, sodium tripolyphosphate, zeolite, sodium citrate, sodium malate, sodium nitrilotriacetate, sodium polyacrylate, sodium carbonate, sodium sulfate, sodium chloride, magnesium sulfate, calcium chloride), a liquid improver (such as glycerol, ethanol, propylene glycol, polyethylene glycol), a thickener (such as carboxymethylcellulose and hydroxyethylcellulose), a flavor, a coloring agent, a germicide, an enzyme, and an anti-inflammatory agent.

The nonionic surfactant according to the present invention shows excellent emulsifying power or solubilizing power to various oils and solvents having a kinematic viscosity of, for example, approximately 0.1 to 3000 mm$^2$/s at 25° C. In particular, the nonionic surfactant according to the present invention can be suitably used as an emulsifier for mineral oils, vegetable oils, aliphatic hydrocarbon-based solvents, alicyclic hydrocarbon-based solvents, and aromatic hydrocarbon-based solvents. Additionally, it can be used as an emulsifier or a dispersant for synthetic resins such as silicones, modified silicones, polyolefins, polyesters, and diene-based polymers (such as polybutadiene), and also as an emulsifier or a solubilizing agent, etc., for essential oils and flavors. Further, it can be suitably used as an emulsifier for emulsion polymerization of monomers such as an acrylic-based monomer, a styrene-based monomer, a diene-based monomer, and a vinyl-based monomer.

Moreover, the nonionic surfactant according to the present invention is capable of showing a highly excellent performance as a detergent in various applications and fields. Examples thereof include a detergent for industrial use and business use and an automotive detergent, a chemical product for processes in industrial fields (such as a fiber refining agent, a metal surface treatment, a metal degreasing agent, a detergent for metal components, a detergent for electronic components, a detergent for leather, a pitch control agent, a detergent for linen supply-related matters, and an additive for dry cleaning), a detergent for kitchens, a detergent for hands and fingers, a detergent for skin, and a detergent for hair. In particular, the nonionic surfactant according to the present invention is capable of showing a highly excellent detergency to stains caused by an adhesion of inorganic matters, wax, and resins in addition to mineral oil stains and vegetable oil stains.

The nonionic surfactant according to the present invention is capable of maintaining stable surface active power for long period of time and preventing a phase separation from taking place with time. Further, the nonionic surfactant according to the present invention contains polyglycerol monoether (of 75 weight % or more, for example) represented by the above formula (1), and thus an amount used of the surfactant can be kept to minimum, which can consequently reduce problems such as environmental pollution and rough dry skin caused by an excessive use of the surfactant.

[Emulsifier, Solubilizing Agent, Emulsifier for Emulsion Polymerization, Detergent]

The nonionic surfactant according to the present invention has the above characteristics, and thus, it can be suitably used as an emulsifier, a solubilizing agent, an emulsifier for emulsion polymerization, and a detergent, for example.

An emulsifier, a solubilizing agent, an emulsifier for emulsion polymerization, or a detergent of the present invention contains at least the above nonionic surfactant. A proportion of polyglycerol monoether represented by the formula (1) is, for example, 75 weight % or more, preferably 80 weight % or more, particularly preferably 85 weight % or more, relative to a total amount of non-volatile contents (100 weight %) of the emulsifier, the solubilizing agent, the emulsifier for emulsion polymerization, or the detergent of the present invention. An upper limit of the proportion is 100 weight %.

The emulsifier, the solubilizing agent, the emulsifier for emulsion polymerization, or the detergent of the present invention may contain polyglycerol, and a content of polyglycerol is, for example, 20 weight % or less, preferably 10 weight % or less, relative to the total amount of non-volatile contents (100 weight %) of the emulsifier, the solubilizing agent, the emulsifier for emulsion polymerization, or the detergent of the present invention. When the content of polyglycerol exceeds the above range, the emulsifier, the solubilizing agent, the emulsifier for emulsion polymerization, or the detergent of the present invention tends to have low dispersibility to water.

The emulsifier, the solubilizing agent, the emulsifier for emulsion polymerization, or the detergent of the present invention may further contain polyglycerol polyether such as polyglycerol diether and polyglycerol triether, and a content of polyglycerol polyether is, for example, 5 weight % or less, preferably 1 weight % or less, relative to the total amount of non-volatile contents (100 weight %) of the emulsifier, the solubilizing agent, the emulsifier for emulsion polymerization, or the detergent of the present invention. When the content of polyglycerol polyether exceeds the above range, the emulsifier, the solubilizing agent, the emulsifier for emulsion polymerization, or the detergent of the present invention tends to have low dispersibility to water.

EXAMPLES

The present invention will be described in more details in the following examples. However, the present invention is not limited to these examples. Resultant compounds are analyzed by the following method.
(1) HPLC Analysis Conditions
HPLC device: Waters2690 (manufactured by Waters corporation)
Column: Wakosil 5C18 (manufactured by FUJIFILM Wako Pure Chemical Corporation (formerly manufactured by Wako Pure Chemical Corporation); a reversed phase partition column having an octadecylsilyl group as a functional group)
Developing solvent: methanol
Flow rate: 0.5 mL/min
Temperature of column oven: 40° C.
Detection method: RI
Concentration of sample: 5% (solvent: methanol)
Amount poured: 10 µL A retention time for each component is 6 minutes for polyglycerol, 10 to 25 minutes for polyglycerol mono-tocopheryl ether, and 28 to 40 minutes for polyglycerol di-tocopheryl ether.

Production Example 1

430.79 g (1.0 mol) of dl-α-tocopherol and 4.08 g (0.05 mol) of sodium hydroxide were charged into a four-necked flask. Next, a pressure in the flask was reduced to 10 mmHg with an aspirator while heating to 100° C. for 90 minutes for the purpose of removing a water content from a reaction system. After that, the reaction system was brought back to an atmospheric pressure, and 740.08 g (10 mol) of glycidol was dropped for 20 hours under a nitrogen atmosphere while sufficiently stirring a reaction liquid and maintaining a reaction temperature at 130° C. The reaction liquid was then neutralized to pH7 by adding 85 weight % of a phosphoric acid solution. The pressure of the reaction system was again reduced while heating to remove a low-boiling component by distillation, and then a neutralized salt was filtered out to produce a reaction liquid (1).

An average number of glycerol monomers (n) of a compound in a resultant reaction liquid (1) was approximately 10.1 (determined by $^1$H-NMR analysis).

The reaction liquid (1) was separated by HPLC (high performance liquid chromatography), and a peak area was calculated by an infrared radiation absorption detector. An area ratio of polyglycerol to polyglycerol mono-tocopheryl ether (the former:the latter) was 6.5:93.5, and a polyglycerol di-tocopheryl ether content was 0.5% or less (below a detection limit).

Example 1

0.4 g of the reaction liquid (1) (a polyglycerol mono-tocopheryl ether content: 95 weight %) produced in Production Example 1 and 4.0 g of a silicon oil as an oil to be emulsified (dimethylpolysiloxane, a kinematic viscosity at 25° C.: 1000 mm$^2$/s) were charged into a graduated test tube and stirred for 30 seconds with a touch mixer for a test tube (manufactured by IWAKI CO., LTD.). 5.6 mL of distilled water having a temperature of 25° C. was subsequently added thereto, and a resultant solution was further stirred for 1 minutes with the touch mixer for a test tube and then left it standing for 2 hours. An amount of water separated (mL) was measured with the scale on the test tube to calculate emulsifying power (%) based on the following formula (5).

$$\text{Emulsifying power (\%)}=[\text{Amount of water charged (5.6 mL)}-\text{Amount of water separated (mL)}]/\text{Amount of water charged (5.6 mL)}\times100 \qquad (5)$$

Comparative Example 1

The emulsifying power (%) was calculated in the same manner as in Example 1 except that polyglycerol monoisostearyl ether (manufactured by Dicel Corporation, a monoether body content: 90 weight %, an average number of glycerol monomers: approximately 10.3) was used instead of the reaction liquid (1) produced in Production Example 1.

Comparative Example 2

The emulsifying power (%) was calculated in the same manner as in Example 1 except that polyglycerol monolauryl ether (manufactured by Dicel Corporation, a monoether body content: 94 weight %, an average number of glycerol monomers: approximately 4.1) was used instead of the reaction liquid (1) produced in Production Example 1.

Comparative Example 3

The emulsifying power (%) was calculated in the same manner as in Example 1 except that polyoxyethylene isocetyl ether (trade name "EMALEX 1605", manufactured by Nihon Emulsion Co., Ltd.) was used instead of the reaction liquid (1) produced in Production Example 1.

Comparative Example 4

The emulsifying power (%) was calculated in the same manner as in Example 1 except that polyoxyethylene isostearyl ether (trade name "EMALEX 1805", manufactured by Nihon Emulsion Co., Ltd.) was used instead of the reaction liquid (1) produced in Production Example 1.

The results of Example 1, Comparative Examples 1 to 4 were shown together in the following table.

Example 2

The emulsifying power (%) of the reaction liquid (1) was calculated in the same manner as in Example 1 except that 4.0 g of liquid paraffin (a kinematic viscosity at 25° C.: 9.8 mm$^2$/s) was used as the oil to be emulsified.

Example 3

The emulsifying power (%) of the reaction liquid (1) was calculated in the same manner as in Example 1 except that 4.0 g of an olive oil (a kinematic viscosity at 25° C.: 80.1 mm$^2$/s) was used as the oil to be emulsified.

The results of Examples 1, 2, and 3 are shown together in the following table.

TABLE 2

| | Emulsifying power (%) | | |
|---|---|---|---|
| Lapsed days (day(s)) | Example 1 (Silicon oil) | Example 2 (Liquid paraffin) | Example 3 (Olive oil) |
| 0 | 100 | 100 | 100 |
| 1 | 100 | 100 | 100 |
| 5 | 100 | 100 | 100 |
| 10 | 100 | 100 | 100 |
| 20 | 100 | 100 | 100 |
| 30 | 100 | 100 | 100 |
| 40 | 100 | 100 | 100 |
| 60 | 100 | 100 | 100 |

INDUSTRIAL APPLICABILITY

The nonionic surfactant of the present invention contains a combination of a specific hydrophilic group and a specific hydrophobic group, which thus prevents a change in hydrophilicity with a temperature change. Accordingly, the nonionic surfactant of the present invention has an excellent surface active effect (emulsifying power and solubilizing power), which is equivalent to those of alkylphenol ethoxylates such as octylphenol ethoxylate and nonylphenol ethoxylate, on various oils such as a mineral oil, a vegetable oil, and a silicone oil, solvents, and synthetic resins, and is capable of stably maintaining the excellent surface active power for a long time (for example, for 30 days or more, preferably 40 days or more, more preferably 60 days or more). Further, this nonionic surfactant is environmentally friendly. Therefore, the nonionic surfactant of the present invention is useful for a detergent, an emulsifier, an emulsifier for emulsion polymerization, or a solubilizing agent.

TABLE 1

| | Emulsifying power (%) | | | | |
|---|---|---|---|---|---|
| Lapsed days (day(s)) | Example 1 (Polyglycerol monotocopheryl ether) | Comparative Example 1 (Polyglycerol monoisostearyl ether) | Comparative Example 2 (Polyglycerol monolauryl ether) | Comparative Example 3 (Polyoxyethylene isocetyl ether) | Comparative Example 4 (Polyoxyethylene isostearyl ether) |
| 0 | 100 | 100 | 100 | 100 | 100 |
| 1 | 100 | 100 | 100 | 49 | 59 |
| 2 | 100 | 100 | 100 | 25 | 27 |
| 5 | 100 | 100 | 100 | 0 | 0 |
| 10 | 100 | 85 | 100 | 0 | 0 |
| 20 | 100 | 80 | 100 | 0 | 0 |
| 30 | 100 | 70 | 100 | 0 | 0 |
| 40 | 100 | 70 | 95 | 0 | 0 |
| 60 | 100 | 65 | 90 | 0 | 0 |

The invention claimed is:

1. A nonionic surfactant comprising polyglycerol monoether represented by the following formula (1):

[Formula 1]

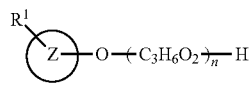

(1)

wherein a ring Z represents a condensed ring of an aromatic hydrocarbon ring having 6 to 14 carbon atoms and a 3 to 6-membered heterocycle containing an oxygen atom as a heteroatom; $R^1$ is a substituent bonded to the ring Z and represents an aliphatic hydrocarbon group having 14 to 25 carbon atoms; the ring Z optionally has one or more substituents other than $R^1$; and n is an average number of monomers of glycerol and represents 2 to 20.

2. The nonionic surfactant according to claim 1, wherein $R^1$ is a substituent bonded to a heterocycle moiety of the ring Z, the ring Z being a condensed ring of an aromatic hydrocarbon ring having 6 to 14 carbon atoms and a 3 to 6-membered heterocycle containing an oxygen atom as a heteroatom.

3. The nonionic surfactant according to claim 1, wherein the polyglycerol monoether represented by the formula (1) is a compound represented by the following formula (1-1) or (1-2):

[Formula 2]

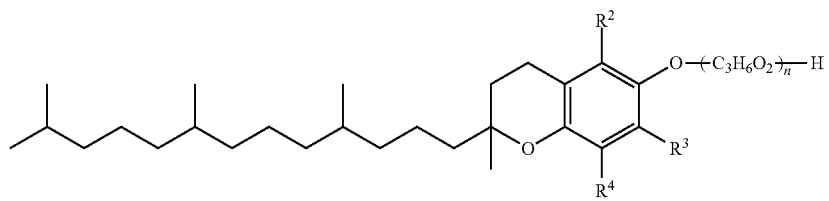

(1-1)

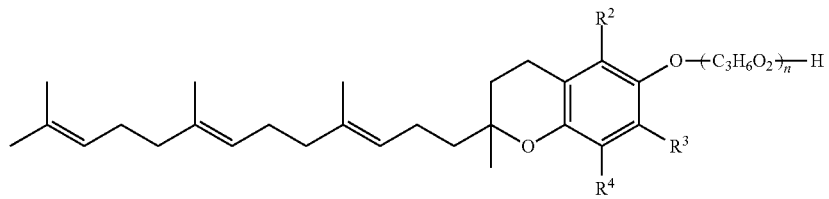

(1-2)

wherein $R^1$, $R^3$, and $R^4$ are the same or different from each other, and each represents a hydrogen atom, an alkyl group having 1 to 5 carbon atoms, or a hydroxy group; and n is an average number of monomers of glycerol and represents 2 to 20.

4. The nonionic surfactant according to any one of claims 1 to 3, for use as a detergent.

5. The nonionic surfactant according to any one of claims 1 to 3, for use as an emulsifier.

6. The nonionic surfactant according to any one of claims 1 to 3, for use as an emulsifier for emulsion polymerization.

7. The nonionic surfactant according to any one of claims 1 to 3, for use as a solubilizing agent.

* * * * *